(12) United States Patent
Hanina et al.

(10) Patent No.: US 10,116,903 B2
(45) Date of Patent: *Oct. 30, 2018

(54) APPARATUS AND METHOD FOR RECOGNITION OF SUSPICIOUS ACTIVITIES

(71) Applicant: AIC Innovations Group, Inc., New York, NY (US)

(72) Inventors: Adam Hanina, New York, NY (US); Lei Guan, Philadelphia, PA (US); Dehua Lai, Brooklyn, NY (US)

(73) Assignee: AIC Innovations Group, Inc., New York, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/831,555

(22) Filed: Mar. 14, 2013

(65) Prior Publication Data

US 2014/0184772 A1    Jul. 3, 2014

Related U.S. Application Data

(63) Continuation-in-part of application No. 13/235,387, filed on Sep. 18, 2011, now Pat. No. 9,875,666, and
(Continued)

(51) Int. Cl.
*H04N 7/18* (2006.01)
*G06F 19/00* (2018.01)
*G09B 19/00* (2006.01)

(52) U.S. Cl.
CPC .......... *H04N 7/18* (2013.01); *G06F 19/3418* (2013.01); *G06F 19/3456* (2013.01); *G09B 19/00* (2013.01)

(58) Field of Classification Search
CPC .................. G09B 23/28; H04N 7/18
(Continued)

(56) References Cited

U.S. PATENT DOCUMENTS

| | | |
|---|---|---|
| 3,814,845 A | 6/1974 | Hurlbrink et al. |
| 5,065,447 A | 11/1991 | Barnsley et al. |

(Continued)

FOREIGN PATENT DOCUMENTS

| | | |
|---|---|---|
| WO | WO 2004/103232 | 12/2004 |
| WO | 2008/070759 A2 | 6/2008 |

(Continued)

OTHER PUBLICATIONS

Danya International, Inc., *Pilot Study Using Cell Phones for Mobile Direct Observation Treatment to Monitor Medication Comgliance of TB Patients*, Mar. 20, 2009, www.danya.com/MDOT.asg.
(Continued)

*Primary Examiner* — Thomas Hong
(74) *Attorney, Agent, or Firm* — Fish & Richardson P.C.

(57) ABSTRACT

A medication confirmation method and apparatus. The method of an embodiment of the invention includes the steps of capturing one or more video sequences of a user administering medication by a video capture device, storing the captured one or more video sequences to a non-transitory memory, and analyzing at least one of the stored video sequences to determine one or more indications of suspicious activity on behalf of the user.

19 Claims, 5 Drawing Sheets

Related U.S. Application Data a continuation-in-part of application No. 12/815,037, filed on Jun. 14, 2010, now Pat. No. 9,293,060, and a continuation-in-part of application No. 13/189,518, filed on Jul. 24, 2011.

(60) Provisional application No. 61/498,576, filed on Jun. 19, 2011, provisional application No. 61/331,872, filed on May 6, 2010, provisional application No. 61/495,415, filed on Jun. 10, 2011.

(58) Field of Classification Search
USPC .................................. 434/262, 365; 348/77
See application file for complete search history.

(56) References Cited

U.S. PATENT DOCUMENTS

| | | |
|---|---|---|
| 5,441,047 A | 8/1995 | David et al. |
| 5,486,001 A | 1/1996 | Baker |
| 5,544,649 A | 8/1996 | David et al. |
| 5,544,661 A | 8/1996 | Davis |
| 5,564,429 A | 10/1996 | Bornn |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brudny et al. |
| 5,911,132 A | 6/1999 | Sloane |
| 5,961,446 A | 10/1999 | Beller et al. |
| 6,126,449 A | 10/2000 | Burns |
| 6,141,584 A | 10/2000 | Rockwell |
| 6,151,521 A | 11/2000 | Guo et al. |
| 6,154,558 A | 11/2000 | Hsieh |
| 6,233,428 B1 | 5/2001 | Fryer |
| 6,283,761 B1 | 9/2001 | Joao |
| 6,302,844 B1 | 10/2001 | Walker |
| 6,327,497 B1 | 12/2001 | Kirchgeorg |
| 6,380,858 B1 | 4/2002 | Yarin et al. |
| 6,409,661 B1 | 6/2002 | Murphy |
| 6,421,650 B1 | 7/2002 | Goetz et al. |
| 6,461,162 B1 | 10/2002 | Reitman et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Eshelman et al. |
| 6,705,991 B2 | 3/2004 | Bardy |
| 6,879,970 B2 | 11/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,369,919 B2* | 5/2008 | Vonk et al. .................. 700/236 |
| 7,395,214 B2 | 7/2008 | Shillingburg |
| 7,415,447 B2 | 11/2008 | Shiffman et al. |
| 7,447,333 B1 | 11/2008 | Masticola et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,740,013 B2* | 6/2010 | Ishizaki et al. .......... 128/204.21 |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,840,277 B2 | 11/2010 | Matos |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,956,727 B2 | 6/2011 | Loncar |
| 7,983,933 B2* | 7/2011 | Karkanias et al. .............. 705/2 |
| 8,321,284 B2 | 11/2012 | Clements et al. |
| 8,702,606 B2 | 4/2014 | Wang |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0027507 A1 | 3/2002 | Yarin et al. |
| 2002/0093429 A1* | 7/2002 | Matsushita ........... A61J 7/0481 340/573.1 |
| 2002/0143563 A1* | 10/2002 | Hufford et al. .................... 705/1 |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2004/0168951 A1* | 9/2004 | Mackie, Jr. ................ A61J 1/03 206/534 |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0008112 A1 | 1/2007 | Covannon et al. |
| 2007/0008113 A1 | 1/2007 | Spoonhower et al. |
| 2007/0016443 A1* | 1/2007 | Wachman et al. ................ 705/2 |
| 2007/0030363 A1 | 2/2007 | Cheatle et al. |
| 2007/0118054 A1* | 5/2007 | Pinhas et al. ................. 600/587 |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1* | 10/2007 | Wehba et al. .................... 705/3 |
| 2007/0265880 A1 | 11/2007 | Bartfeld et al. |
| 2007/0273504 A1 | 11/2007 | Tran |
| 2007/0276270 A1* | 11/2007 | Tran ............................. 600/508 |
| 2008/0000979 A1 | 1/2008 | Poisner |
| 2008/0162192 A1 | 3/2008 | Vonk et al. |
| 2008/0086533 A1* | 4/2008 | Neuhauser et al. .......... 709/206 |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0138604 A1 | 6/2008 | Kenney et al. |
| 2008/0140444 A1* | 6/2008 | Karkanias et al. .............. 705/2 |
| 2008/0178126 A1 | 7/2008 | Beeck et al. |
| 2008/0201174 A1* | 8/2008 | Ramasubramanian et al. .. 705/3 |
| 2008/0219493 A1 | 9/2008 | Tadmor |
| 2008/0238666 A1 | 10/2008 | Loncar |
| 2008/0275738 A1 | 11/2008 | Shillingburg |
| 2008/0279420 A1 | 11/2008 | Masticola et al. |
| 2008/0281630 A1* | 11/2008 | Sekura ............................. 705/2 |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0024112 A1 | 1/2009 | Edwards et al. |
| 2009/0043610 A1 | 2/2009 | Nadas et al. |
| 2009/0048871 A1 | 2/2009 | Skomra |
| 2009/0058635 A1 | 3/2009 | LaLonde et al. |
| 2009/0095837 A1 | 4/2009 | Lindgren |
| 2009/0128330 A1 | 5/2009 | Monroe |
| 2009/0149721 A1 | 6/2009 | Yang |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1* | 2/2010 | Bartfeld ........................... 705/2 |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |

(56) References Cited

U.S. PATENT DOCUMENTS

| | | | |
|---|---|---|---|
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina et al. |
| 2011/0141009 A1 | 6/2011 | Izumi |
| 2011/0153360 A1 | 6/2011 | Hanina et al. |
| 2011/0161109 A1 | 6/2011 | Pinsonneault et al. |
| 2011/0195520 A1 | 8/2011 | Leider et al. |
| 2011/0275051 A1 | 11/2011 | Hanina et al. |
| 2012/0009555 A1 | 1/2012 | Hanina |
| 2012/0075464 A1 | 3/2012 | Derenne et al. |
| 2012/0121729 A1 | 5/2012 | Paterson et al. |
| 2012/0316897 A1 | 12/2012 | Hanina et al. |
| 2013/0044196 A1 | 2/2013 | Guan et al. |

FOREIGN PATENT DOCUMENTS

| | | |
|---|---|---|
| WO | WO 2011/062934 | 5/2012 |
| WO | WO 2012/177524 | 12/2012 |

OTHER PUBLICATIONS

University of Texas, *GuideView*, Mar. 15, 2007, http://www.sahs.uth.tmc.edu/MSriram/GuideView/.
Chen, Pauline W., *Texting as a Health Tool for Teenagers*, The New York Times, Nov. 5, 2009, http://www.nytimes.com/2009/11/05/health/05chen.html?_r=1&emc=.
Whitecup, Morris S., *2008 Patient Adherence Update: New Approaches for Success*, Guideline Trend Report, Oct. 2008.
Osterberg, Lars and Blaschke, Terrence, *Adherence to Medication*, New England Journal of Medicine 2005; 353:487-97, Aug. 4, 2005.
"Global Tuberculosis Control: A short update to the 2009 report", *World Health Organization*, (2009).
"Super-Resolution", *Wikipedia*, (Oct. 5, 2010).
Non-Final Office Action from PTO, U.S. Appl. No. 12/620,686, dated (Dec. 21, 2011),1-78.
Final Office Action from PTO, U.S. Appl. No. 12/620,686, dated (May 8, 2012), 1-24.
Non-Final Office Action from PTO, U.S. Appl. No. 13/558,377, dated (Oct. 22, 2012), 1-21.
Final Office Action from PTO, U.S. Appl. No. 13/558,377, dated May 7, 2013, 1-29.
PCT Search report and written opinion, (PCT/US2010/56935, dated (Jan. 12, 2011),1-9.
International Preliminary Report on Patentability, (PCT/US2010/056935) dated (May 31, 2012), 1-8.
Non-Final Office Action from PTO, U.S. Appl. No. 12/646,383, dated (Dec. 22, 2011),1-78.
Final Office Action from PTO, U.S. Appl. No. 12/646,383, dated (May 8, 2012), 1-31.
Non-Final Office Action from PTO, U.S. Appl. No. 13/558,380, dated (Oct. 4, 2012), 1-20.
Wang et al. "Recent Developments in human motion analysis." Pattern Recognition 36 (220) 585-601 (Nov. 2001).
Final Office Action from PTO, U.S. Appl. No. 13/588,380, dated (Mar. 1, 2013), 1-27.
Non-Final Office Action from PTO, U.S. Appl. No. 12/646,603, dated (Oct. 13, 2011),1-74.
Final Office Action from PTO, U.S. Appl. No. 12/646,603, dated (Feb. 1, 2012), 1-17.
Non-Final Office Action from PTO, U.S. Appl. No. 12/646,603, dated (Jun. 13, 2013), 1-16.
Non-Final Office Action from PTO, U.S. Appl. No. 12/728,721, dated (Jan. 6, 2012), 1-31.
Final Office Action from PTO, U.S. Appl. No. 12/728,721, dated (Apr. 12, 2012), 1-31.
Non-Final Office Action from PTO, U.S. Appl. No. 12/728,721, dated (May 9, 2013), 1-25.
Non-Final Office Action from PTO, U.S. Appl. No. 12/815,037, dated (Mar. 28, 2012),1-17.
Final Office Action from PTO, U.S. Appl. No. 12/815,037, dated (Sep. 13, 2012), 1-15.
Non-Final Office Action from PTO, U.S. Appl. No. 12/815,037, dated (Jul. 18, 2013), 1-19.
PCT Search report and written opinion, (PCT/US2011/35093), dated (Sep. 12, 2011),1-8.
Non-Final Office Action from PTO, U.S. Appl. No. 12/899,510, dated (Jan. 23, 2013), 1-20.
Final Office Action from PTO, U.S. Appl. No. 12/899,510, dated (Aug. 20, 2013).
PCT Search report and written opinion, (PCT/US11/54666), dated (Feb. 28, 2012), 1-13.
Non-Final Office Action from PTO, U.S. Appl. No. 12/898,338, dated (Jun. 19, 2012), 1-16.
Final Office Action from PTO, U.S. Appl. No. 12/898,338, dated Nov. 9, 2012), 1-12.
PCT Search report and written opinion, (PCT/US11/54668), dated Feb. 28, 2012, 1-12.
Non-Final Office Action from PTO, U.S. Appl. No. 13/189,518, dated (Dec. 21, 2012), 1-10.
Final Office Action from PTO, U.S. Appl. No. 13/189,518, dated (Jul. 23, 2013), 1-16.
PCT Search report and written opinion, (PCT/US12/41785) dated (Aug. 17, 2012),1-10.
Non-Final Office Action from PTO, U.S. Appl. No. 13/235,387, dated Sep. 12, 2013), 1-16.
PCT Search report and written opinion, (PCT/US12/42843), dated (Aug. 31, 2012), 1-8.
PCT Search report and written opinion, (PCT/US2012/051554), dated (Oct. 19, 2012), 1-12.
Huynh et al., "Real time detection, tracking and recognition of medication intake." World Academy of Science, Engineering and Technology 60 (2009), 280-287.
PCT Search report and written opinion, (PCT/US12/59139), dated (Dec. 18, 2012), 1-15.
PCT Search report and written Opinion, PCT/US13/20026, dated (Aug. 5, 2013), 1-14.
Ammouri, S.; Biloduau, G. -A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Dec. 18, 2013] Retrieved from ProQuest Technology Collection.
Mintchell, "Exploring the Limits of Machine Vision", Automating World, Oct. 1, 2011.
EPO Search Report for Application No. 14770974.5, dated Aug. 30, 2016, (4 pages).
U.S. Appl. No. 12/815,037, filed Jun. 14, 2010, Hanina et al.
U.S. Appl. No. 15/048,798, filed Feb. 19, 2016, Hanina et al.
U.S. Appl. No. 13/235,387, filed Sep. 18, 2011, Hanina et al.
U.S. Appl. No. 13/674,459, filed Nov. 12, 2012, Hanina et al.
SIPO Office Action for CN App. No. 2014800143728, dated Jul. 31, 2017 (9 pages).
CN Office Action for CN App No. 201480014372.8 dated Aug. 2, 2018 (with English translation) (21 pages).

* cited by examiner

APPARATUS AND METHOD FOR RECOGNITION OF SUSPICIOUS ACTIVITIES

CROSS REFERENCE TO RELATED APPLICATIONS

This application is Continuation In Part application of U.S. patent application Ser. No. 13/235,387, filed Sep. 18, 2011 to Hanina et al., titled APPARATUS AND METHOD FOR RECOGNITION OF PATIENT ACTIVITIES, which claims the benefit of U.S. Provisional Patent Application Ser. No. 61/498,576, filed Jun. 19, 2011 to Hanina et al., titled APPARATUS AND METHOD FOR RECOGNITION OF PATIENT ACTIVITIES, the entire contents of each of these applications being incorporated herein by reference. This application is also a Continuation in Part Application of U.S. patent application Ser. No. 12/815,037, filed Jun. 14, 2010 to Hanina et al., titled APPARATUS AND METHOD FOR RECOGNITION OF PATIENT ACTIVITIES WHEN OBTAINING PROTOCOL ADHERENCE DATA, which claims the benefit of U.S. Provisional Patent Application Ser. No. 61/331,872, filed May 6, 2010, to Hanina et al., titled APPARATUS AND METHOD FOR RECOGNITION OF PATIENT ACTIVITIES WHEN OBTAINING PROTOCOL ADHERENCE DATA, the entire contents of each of these applications being incorporated herein by reference. This application is also a Continuation In Part application of U.S. patent application Ser. No. 13/189,518, filed Jul. 24, 2011 to Hanina et al., titled METHOD AND APPARATUS FOR MONITORING MEDICATION ADHERENCE, which claims the benefit of U.S. Provisional Patent Application Ser. No. 61/495,415, filed Jun. 10, 2011 to Hanina et al., titled METHOD AND APPARATUS FOR MONITORING MEDICATION ADHERENCE, the entire contents of each of these applications being incorporated herein by reference.

FIELD

This invention relates generally to patient compliance in medication administration protocol scenarios including ingestion of medication, and more particularly to an apparatus and method for the collection, analysis and transmission of data related to patient movements related to such medication administration and ingestion of the medication into the body of a user, placing the medication in their mouth, or other method of transferring medication into their body, including features for identifying suspicious or purposefully malicious activity on the part of the patient.

BACKGROUND

Dr Lars Osterberg, M.D. and Dr, Terence Blaschke have reported in the New England Journal of Medicine, Adherence to Medication, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." Adherence, p. 487. The authors conclude "Poor adherence to medication regimens is common, contributing to substantial worsening of disease, death and increased healthcare costs." Adherence, p. 494. The Trend Repot Series, 2008 Patient Adherence Update: New Approaches for Success, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication. As has been shown in regards to various public health medication administration situation, such as administration of tuberculosis medication by the WHO, Directly Observed Treatment (DOT) improves compliance of patients. Global Tuberculosis Control: A Short Update to the 2009 Report, World Health Organization, 2009. As is shown in this report, funding for implementing DOT programs is high. Thus, the ability to implement such a program with less of a financial burden would be desirable.

Traditionally, participants attend introductions and follow ups for clinical trials in-person. Other patients outside of the clinical trial setting attempting to adhere to a particular medication protocol similarly are given a prescription and a particular set of instructions from a prescribing medical provider or prescribing doctor. Compliance is then measured at a next visit with that prescribing professional through traditional methods of counting unused medication, and patient interviews. Thus, data collection is similarly limited to patient visits, rather than on a daily basis. These old methods such as patient questioning and medication counting have been proven to be inadequate measures of adherence and offer no information on dose timing and drug holidays (omission of medication for three or more sequential days).

Compliance and medication adherence technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times. This problem is even more acute when a participant is performing a suspicious action, or is otherwise maliciously avoiding taking their medication.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp 1, 763-767, October 2003. To date, technologies alone have only been used to monitor compliance rather than to encourage it. These technologies also provide no specific defense against patients who are purposefully not taking their medication.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact properly administering required medication, including placing a medication pill into their mouth, or injecting or inhaling medication following a predetermine series of steps as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, purposefully avoiding taking their medication, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Furthermore, this system is expensive and requires constant maintenance to confirm that the various mechanical parts are in working order. Finally, there is no consideration of participants who may be trying to trick the system and purposefully avoid taking their medication as may be the case in various patient populations such as schizophrenia populations, prison populations, or other groups.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence, including ingestion, inhalation, injection of the medication, or the relationship of adherence to the efficacy or safety of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration or population management. This once again thus fails to defend against suspicious or malicious medication users who purposefully do not take their medications.

Therefore, it would be desirable to provide an apparatus that overcomes the drawbacks of the prior art.

SUMMARY

In U.S. patent application Ser. No. 12/620,686, filed Nov. 18, 2009, titled Method and Apparatus for Verification of Medication Administration Adherence; currently pending, U.S. patent application Ser. No. 12/646,383, filed Dec. 23, 2009, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; and U.S. patent application Ser. No. 12/728,721, filed Mar. 22, 2010, titled Apparatus and Method for Collection of Protocol Adherence Data, currently pending, the contents of these four applications being incorporated herein by reference, the inventors of the present invention have proposed a system, method and apparatus that allow for complete control and verification of adherence to a prescribed medication protocol or machine or apparatus use in a clinical trial setting, whether in a health care provider's care, or when self administered in a homecare situation by a patient.

These applications present the only medication management system that may determine whether a user is actually following a protocol, provide additional assistance to a user, starting with instructions preferably including one or more interactive and real-time audio, visual textual or the like prompts based upon one or more actions detected of the user, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings.

The inventive solution builds on these initial inventions and provides one or more features that may be employed in accordance with these systems to detect suspicious activity of a user, and to thwart users who purposefully do not take their medication. The inventive system may visually and audibly recognize a fixed series of actions, each comprising part of the medication administration process, and may further recognize deviations from the fixed series of actions, whether audio, video, and whether used for monitoring orally ingested, injectable, inhalable or other administered medications. The system may also interact in real-time with the patient when something is identified as incorrect, wrong or suspicious and either prompt a different action or raise an alert and recommend an intervention by a healthcare provider.

In accordance with an embodiment of the present invention, a motion capture procedure for capturing motion information related to the administration of pill or film based oral medications, or injectable, inhaler-based, other non-pill based medication, or any other form of patient administration task that may be performed, may be utilized in accordance with one or more of the inventions noted in the above-referenced applications. Therefore, in accordance with an embodiment of the present invention, a method and apparatus may be provided for analyzing captured patient motion data, preferably in near real time to provide feedback to the user, to determine a number of times a participant performs some action that is considered suspicious. Additionally, the patient performance information may be analyzed asynchronously to determine other features of data that may suggest some malicious intent on the part of the patient.

Further in accordance with an embodiment of the present invention, one or more predetermined motion sequences may be determined, and one or more related errors or other suspicious activities may be defined related to each of these one or more motion sequences. The automated system of the invention may then monitor a number of times these one or more suspicious activities may take place during a medication administration, and over multiple administrations in order to determine a pattern of potentially suspicious behavior over time.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
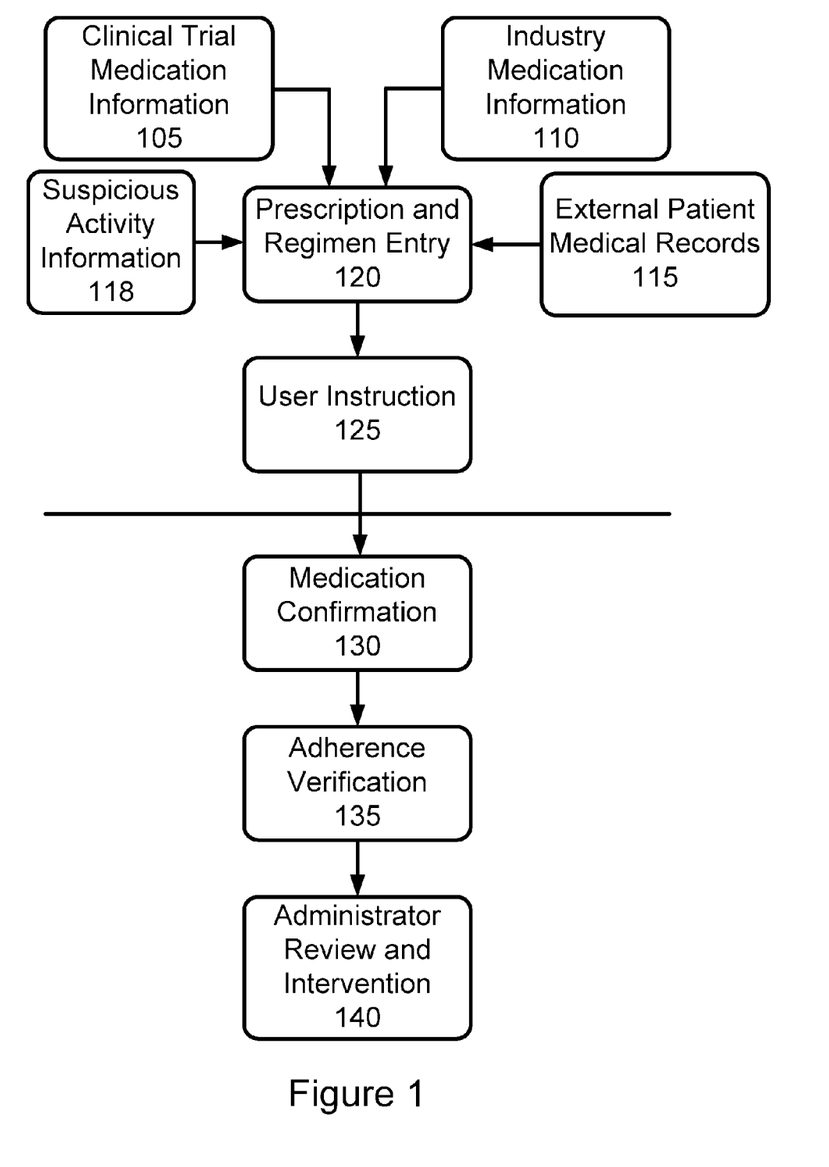
FIG. 1 is a flow chart diagram depicting a method in accordance with an embodiment of the invention.

The invention will now be described making reference to the following drawings in which like reference numbers denote like structure or steps. Referring to FIG. 1, a data flow overview in accordance with the operation of an embodiment of the present invention is shown. In accordance with this embodiment of the invention, information about a particular drug to be the subject of a clinical trial, to be employed in a public health or disease management situation, or the like, other medication administration program or prescription, or other patient self-administered medical task such as performing a home based urine test or the like may be provided in a database 105, and existing industry medication information databases 110 are preferably employed to access prescription, interaction, application, and other available information about any number of proposed prescription and non-prescription medications and their possible interaction with the clinical trial or other medications. Further, patient medical records 115 may be used, and as will be described below, in conjunction with the industry medical information and a medical professional's prescribing expertise to confirm that a patient is a good candidate for such a clinical trial, or medication administration program. These databases may be accessed in a manner known to one of ordinary skill in the art. This information may further include information related to associated likely typical elements of suspicious or malicious behavior. Such elements may be based upon the type of medication, method of medication administration, demographics or other information about the patient, other features, or a combination of these elements. Suspicious activity information 118 is preferably transferred to the system at this time as well, and as noted above may include one or more indications of patient movements or other actions that may indicate suspicious behavior on behalf of the patient, a malicious intent to trick the system, or actions of other high risk population. The various embodiments of the present invention may also be provided to determine if a patient is performing an action or task correctly or if they are simply making a mistake.

Once confirmed, a medication administration and ingestion or other medication regimen in accordance with the clinical trial or other prescription requirements such as in a public health, medical practice environment or the like may be prescribed and entered into the system of the invention at 120. Such medication administration regimen may include one or more of ingesting or swallowing a pill, using an inhaler device, using an injectable medication device, employing a patch, sublingual administration, a cheek or other skin located medication administration device or the like. Once entered into the system, a particular prescription regimen may cause a set of user instructions, various training sequences and the like 125 to be generated and transmitted to an apparatus provided to a patient in accordance with an embodiment of the invention for access to the system of the invention. Such an apparatus may comprise a custom designed video and audio capture, analysis and transmission apparatus, a smart phone or other mobile device including a camera or other video and audio capture apparatuses, a netbook, laptop computer, desktop computer, tablet device or the like, free standing, or built into a mirror or cabinet or the like, or other computing appliance allowing for the display of instructions to a patient, and allowing for the eventual capture, analysis and transmission of video, audio and other analysis information. When installing software on a user's own hardware system, it is preferred that the software detect and otherwise test or determine that the hardware attempting to be utilized by the patient is sufficient to implement the invention and is sufficient to run a software package provided in accordance with the invention. Thus, the software may check that a camera includes sufficient resolution, that a memory of the device is of sufficient size to allow for sufficient captured video storage, that audio may be properly captured, and that the transmission system includes sufficient bandwidth to transmit and receive captured video, audio, video instructions and the like. Processing may also be performed at a remote location, thus allowing the user to include a lighter application or the like on their local device. Alternatively, the user may employ the local device as a gateway only, all data being transmitted to a remote location for processing, and returning responses as a result of such processing. Thus, a user may be able to dial up a video conference number, or otherwise interact with a remote site, such as by visiting a particular website or URL.

Such user instructions and training sequences may include general instructions about the particular medication subject to the current trial or medication administration protocol, methods for administration, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display of the user apparatus. It is further contemplated that such instructions may indicate one or more movement sequences to be associated with a corresponding one or more medication administration sequences. These instructions preferably indicate proper and improper motions that may be taken by a patient for ingesting a pill, using an inhaler, using an injectable medication, and the like, and may indicate various motions that may or may not be performed by a user. In such a manner, the patient may be instructed to properly perform all requested actions, and avoid actions that may be indicative of a patient trying to trick the system. In an alternative embodiment, it may be possible to particularly not describe to the patient the various suspicious behaviors that will be tracked in an attempt to "trap" the unsuspecting malicious patient. These traps may be maintained and running in a background of the system. Thus, as will be described below, detection of one or more errors may generate real time displayed video and/or audio feedback to the patient in order to correct actions, while one or more other errors may be logged by the system but preferably provide no feedback to the patient, and thus may be accumulated and used to analyze patient actions without providing instructions and help to avoid being caught by the system. After being "caught" a number of times, a state of the user may be changed to one of heightened security awareness. Thus, a user may be first started in a low level of observation. After a predetermined number of potentially actions that are caught, the user may be labeled as a user that is attempting to trick the system, or that is performing one or more suspicious acts, thus warranting a heightened level of security. Additional suspicion will surround review of all actions of the patient. After properly using the system correctly for another predetermined period of time, the user may be returned to the initial normal state. If on the other hand, suspicious activity continues, the user may be moved to yet another state where the user may be recommended to be removed from a clinical trial, or taken off a particular medication, for example.

In accordance with one or more embodiments of the present invention, one or more of these sets of motions or actions may comprise confirmation that a user has placed a pill in their mouth and has properly swallowed the pill correctly and has therefore ingested the medication properly through visual confirmation of location, confirmation that the user has properly used an inhaler device through visual confirmation of position and/or audio confirmation of actuation, confirmation that the user has properly used an injectable device through visual confirmation of position and/or audio confirmation of actuation, or the like.

Referring to the lower portion of FIG. 1, the horizontal line indicates a time for patient administration of medication. At such time, the user may be notified to take their medication through any desirable communication and notification system, including text messaging, email, telephone call, automated calendar reminder or the like. While not explicitly shown, first, preferably the identity of a user may by confirmed through the use of a facial recognition sequence, other biometric identification sequence, voice recognition, other password identification system, or a combination thereof. Other features of use of the system, such as time to turn on, time to perform other tasks, etc. may be recorded to further aid in determining a consistent identity of a user of the system. The user may also be asked to say "hello" or some other word sequence to allow for audio recognition of the voice of the user. Upon recognition of the individual, the system may display one or more data regarding the individual, such as, by way of example only, name, patient status, medication to be administered, calendar indicating to the patient when medication has been administered and if any administration times have been missed, and, selectively, a score indicative of a level of compliance of the individual with the medication protocol, if desired. Other metrics may also be tracked, such as if too many skips have been registered by a user, or if too many self reports that the user has taken their medication without the user of the automated system, each indicating potentially suspicious activity. This identification information may be stored to a remote location to aid in determining whether a particular user is registering at more than one site, with more than one device, and thus attempting to be paid twice for the trial. Such patients are unlikely to be interested in taking the medication at all. Additional attributes of a patient may also be stored in a centralized database or the like to potentially alert other clinical trials of potential offenders. Thus, one or more patient behavior profiled, facial identification characteristics voice recognition, combination thereof, may allow one or more subjects to be placed or a watch list or the like after having been identified as non-compliers. Thus, patients trying to get medication from multiple clinics, patients trying to sign up for multiple clinical trials, or patients trying to sign up at multiple sites in a single clinical trial may be recognized and determined before being able to be engaged at these other sites.

The system shall preferably be able to learn the pattern of suspicious patients based on all data collected (such as number of misses, number of skips, manual ratios, time on tasks, number of usability errors, number of suspicious errors, study coordinator/sponsors notes, flags, video reviewing results.). Then a patient can be easily classified as suspicious level 1, level 2 . . . or not by checking whether the patient fits in certain pattern. The machine will keep learning each day when more data are gathered and more patients are enrolled. Thus, a more accurate placement of the user in a particular state in a state machine, a will be described below, can be more accurately determined.

Once identified and notified of a type of medication to be administered, the patient may display a medication, such as a pill, dissolvable film or the like, administration apparatus, such as an inhaler, injectable apparatus, or other medication form (including a pill bottle or the like) to confirm that the medication is correct and is the currently prescribed medication to be taken through the use of text recognition, medication recognition, barcode or other code reading of one or more unique identifiers from the administration apparatus, pill bottle or the like, or other appropriate medication recognition scheme. One or more confidence level measurements may be employed, such as that described in co-pending application Ser. No. 13/110,500 filed May 18, 2011 to Guan et al., titled Method and Apparatus for Pattern Tracking, the entire contents thereof being incorporated herein by reference.

In addition to recognizing the pill or other medication, the system may preferably track how patient holds the pill or other medication, and further may track continuous motion from hand to mouth to confirm that no suspicious action has taken place. Thus, the system may also check consistent hand usage between identification of the pill and placing the pill in the mouth of the user. In addition to tracking the motion of the hand, if the user is to take the pill out of a blister pack, the user may track a motion sequence for tracking complete gestures on screen from taking out of the pill bottle or blister pack all the way to placing in mouth/ingesting, drinking water, showing and tracking water go down, swallowing, and even showing empty mouth so that any deviation from the desired sequence may be identified as a potentially suspicious activity. Furthermore, the system may view the blister pack to determine if the correct number of pills have been removed, that the correct number of pills are remaining, and whether other pills or the like have been removed that should not have been removed. Such suspicious activity may be used to automatically flag potentially suspicious activity.

Thereafter, the patient may be instructed to administer the medication in the prescribed manner. One or more of these administration sequences may comprise confirmation that a user has placed a pill in their mouth (ingested the pill) through visual confirmation of location, confirmation that the user has properly used an inhaler device through visual confirmation of position and/or audio confirmation of actuation, confirmation that the user has properly used an injectable device through visual confirmation of position and/or audio confirmation of actuation. Thus, for an oral administration, the user may be asked to place the pill in their mouth, show the pill in their mouth to the camera to confirm its presence, drink a glass of water, and show an empty mouth to the camera to confirm the pill is gone. The user may be asked to change the position of their tongue relative to the pill to provide a more complete view of the pill in the mouth of the user to the camera. For example, if the user only presents the top of their tongue to the camera, and refuses to show under their tongue, a suspicious activity may be flagged. Improper tilting of the glass of water, or the head of the user when drinking the water may be further automatically recognized and provided as potentially suspicious activity, thus changing the state of the user and perhaps changing a level of scrutiny for reviewing activity of the user. Swallowing motions may also be confirmed, the absence thereof providing further evidence of potentially suspicious or malicious behavior. For an inhaler, the user may be asked to properly position the inhaler and show the positioning to the camera, to actuate the inhaler in view of the camera, to breathe in view of the camera, and to hold their breath for a predetermined period of time in front of the camera. Different sounds, for example different frequencies emitted from the inhaler, may suggest that the user may be blocking the aerosol or power of the inhaler with their teeth, either in error or on purpose. Such incorrect positioning may suggest incorrect placement, and therefore incorrect medication administration. For an injectable medication the user may be asked to show the medication to the camera, to place the injectable medication adjacent the proper body part to receive the injection in view of the camera, to actuate the injectable medication in view of the camera, and the like.

During this administration, monitoring of the various indicated potentially suspicious activities may be provided. Thus, as described above, a determination of whether the head or face of the patient leaves the field of view of the camera may be determined, and as will be described below, a state of the user may be changed based upon this or other suspicious activities noted in accordance with this application. Other suspicious activities that may be tracked may include the patient covering their mouth with their hand during medication administration of a pill based medication, other body movements indicating an attempt to remove the medication or the like. Furthermore, audio recognition may also be employed to determine whether the patient is spitting out a pill, for example, or to assist in determining whether an inhalable or injectable medication has been properly actuated. Each of these features may be preferably monitored over time so that while a single indication of potentially suspicious behavior provides important information, continued performance of such suspicious behavior will provide a more complete picture of attempts to trick the system, thus allowing for intervention to identify the patient, and address the suspicious behavior. Different actions performed on the part of the user may allow the user to be classified into one or more states, the state being changed based upon one or more actions they may perform over time. Such a state machine may be performed in accordance with one or more features as described in copending U.S. patent application Ser. No. 13/189,516, filed Jul. 24, 2011 to Hanina et al., titled Method and Apparatus for Monitoring Medication Adherence, the contents thereof being incorporated by reference. The medication administration states noted therein may be employed to classify suspicious users based upon their actions.

If a medication is being used to treat a certain symptom, therefore in accordance with one or more embodiments of the invention, the system may be employed to measure visually if that symptom is improving. For example, concentration, speed to complete tasks, motor control etc. If symptoms or behavior (eye movement still erratic for example) fail to improve, this may suggest that the user is not taking their medication. Mood may also be measured and monitored as a signal of whether the user is taking their medication. Various actions may once again be used to classify a user in one or more medication administration states, thus suggesting a level of review and follow up that may be required by the system to follow up with the user.

Additionally, determination of movement of the imaging device may be determined, through analysis of information provided in the field of view thereof, or through the use of one or more gyroscopes or accelerometers thereon. Thus, if the user tampers with the position of the imaging device or camera, it will be known and the monitor or healthcare provider may be automatically notified. Other clues, such as changes in a background setting at one or more critical times of medication administration, or other indications of movement of the device, or the like.

After confirmation or failure of confirmation of such administration, the patient may be provided with a progress report regarding how they have performed over time, and further providing encouragement for future adherence. Additionally, notice of a next administration time may be provided, along with one or more messages from a healthcare provider regarding protocol changes, or other desired information. Furthermore, various detected instances of potentially suspicious behavior may be reported to a healthcare provider or the like via a dashboard reporting general adherence information along with the noted suspicious activity information. A warning may also be visually shown to the patient that unusual activity has been detected. They may be told that incorrect use of the medication or protocol may result in their study coordinator/healthcare provider being contacted, their being removed from the trial, or there may be an additional level of monitoring applied to the patient.

Therefore, in accordance with the invention, confirmation of patient adherence to the prescribed administration schedule for the medication as prescribed by the clinical trial or other prescription regimen may be determined, while suspicious or malicious behavior may be identified. While such confirmation may take a number of forms, in accordance with the invention, a preferred method for such confirmation may include capturing a video and audio sequence of the patient actually administering the medication. In a further preferred method, such a sequence for such confirmation may include employing a facial recognition sequence or other biometric confirmation that a particular patient is in fact receiving treatment, but may also provide for the ability to obscure the face or other identifying feature of a user, simplify a displayed image through rotoscoping or the like, or otherwise encrypt such information to allow for the storage and use of such images while protecting the identity of the patient, a technique that may be beneficial when a medication administration manager is providing a general report about a clinical trial, and not trying to remedy a situation with a particular patient, or in particular in a public health or disease management scenario. Activity recognition, gesture recognition, computer vision processing or other feature for determining whether a particular subject movement meets a predefined movement sequence may be employed to be sure that the patient is properly taking prescribed medication. This same gesture recognition may also be employed to determine suspicious or malicious behavior on the part of the user, as described above. Audio recognition may also be employed to determine suspicious noises such as coughing noises or the like at one or more critical key moments associated with medication administration. For example if coughing consistently occurs routinely after the user has pace a medication pill in their mouth, then the patient may be escalated to a state providing for a higher level of scrutiny of review during the administration process over time. Finally, measurement of time on task, indicative of an amount of time required for the user to perform one or more prescribed steps may also be employed to aid in determining suspicious behavior. This time on task may be measured across many different devices and instances of use of the apparatus to determine one or more trends that may be interesting, and may be used to determine suspicious behavior. For example, time on task may be employed to determine miming of an activity that the user I not really performing the medication administration steps as required.

Figure 2:
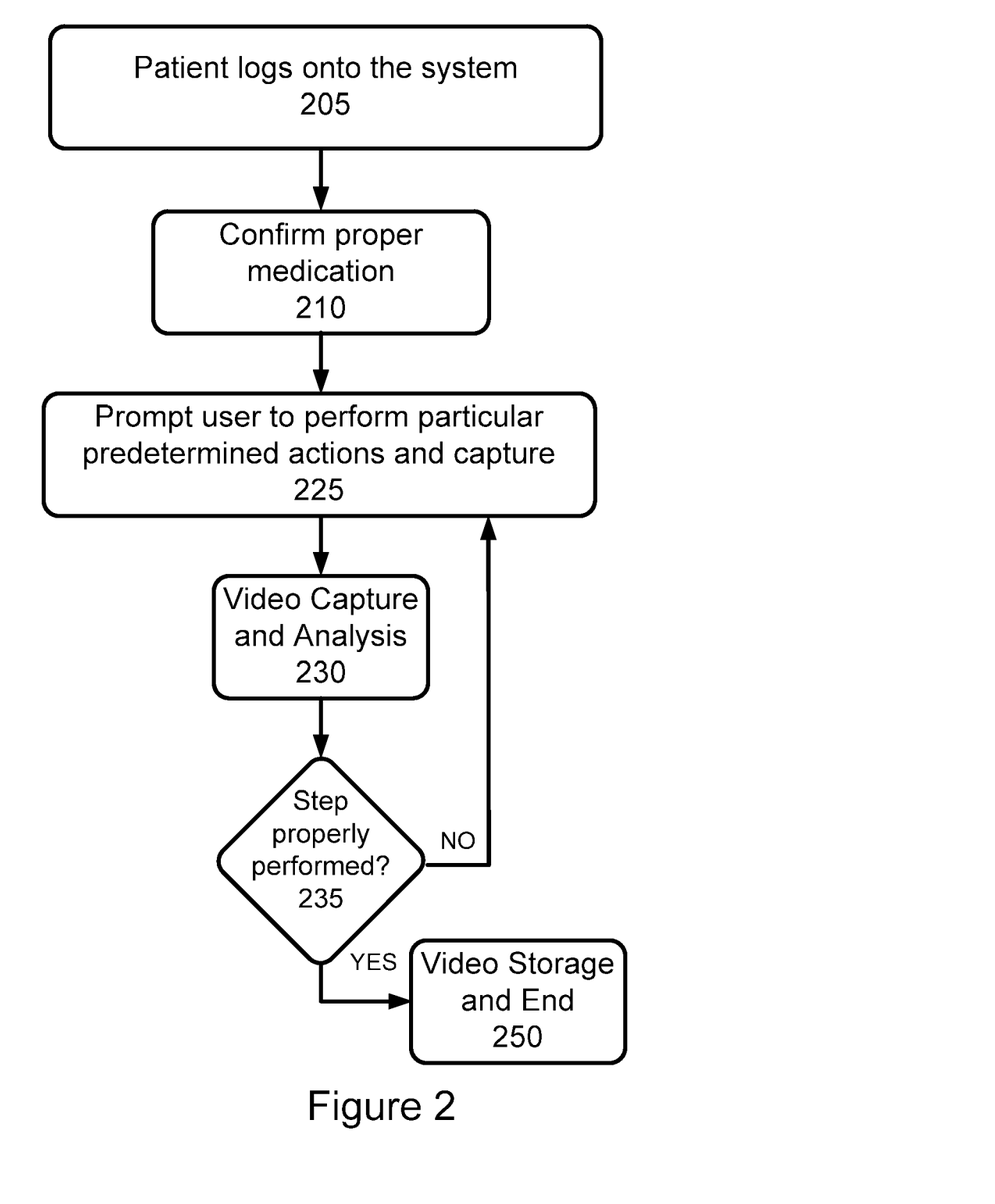
FIG. 2 is a flowchart diagram depicting a video sequence capture method in accordance with an embodiment of the invention.

Referring next to FIG. 2, a method in accordance with an embodiment of the present invention for performing audio and video capture and recognition of adherence to a prescribed protocol, and for determining one or more indications of suspicious or malicious activity, is described, as set forth in steps 130 and 135 of FIG. 1. In FIG. 2, a patient may first log into the system of the invention at step 205, employing the facial recognition, biometric recognition, password entry, voice recognition, or other patient identification method, and at step 210 proper medication is preferably confirmed as noted above, through the use of bar code reading, text recognition, visual recognition employing video or still image recognition, or other medication recognition technique as described above. The patient may be reminded to log onto the system to take their medication through any type of reminder, such as a text message, email, phone call, automated alarm or the like. Processing then passes to step 225 where the user may be prompted to perform one or more predetermined actions, the video and/or audio of each of these actions preferably being captured. Video capture analysis may then begin at step 230, such analysis comprising analysis of the newly captured video and/or audio. At step 235 it may be determined whether the action has been properly captured, and whether the captured action has been properly analyzed by the system in one or more manners as will be described below.

If it is determined that administration of the medication did not take place properly, processing may return to step 225 and the user may be once again prompted to perform the action. (Of course, if this process involves actual administration of pill, film, inhaler, injectable medication, or any other medication, it may not be proper to request re-performance of the action, unless it can be determined that the user did not actually administer the medication.) If the action has been properly performed and is able to be analyzed, processing ends at step 250 where the various captured video sequences are stored. These stored sequences may also be made available for human review and involvement, when it is determined that this would be beneficial, and may further preferably be employed to determine suspicious or malicious activity. Areas of interest for review may be highlighted and marked as potentially including suspicious or incorrect activity. Percentage estimates of risk may be automatically provided by the system based on risk algorithms that are generated by the state machine, and based upon a state into which the user may have been placed based upon their prior activity, and one or more learned activities from a plurality of users.

Figure 3:
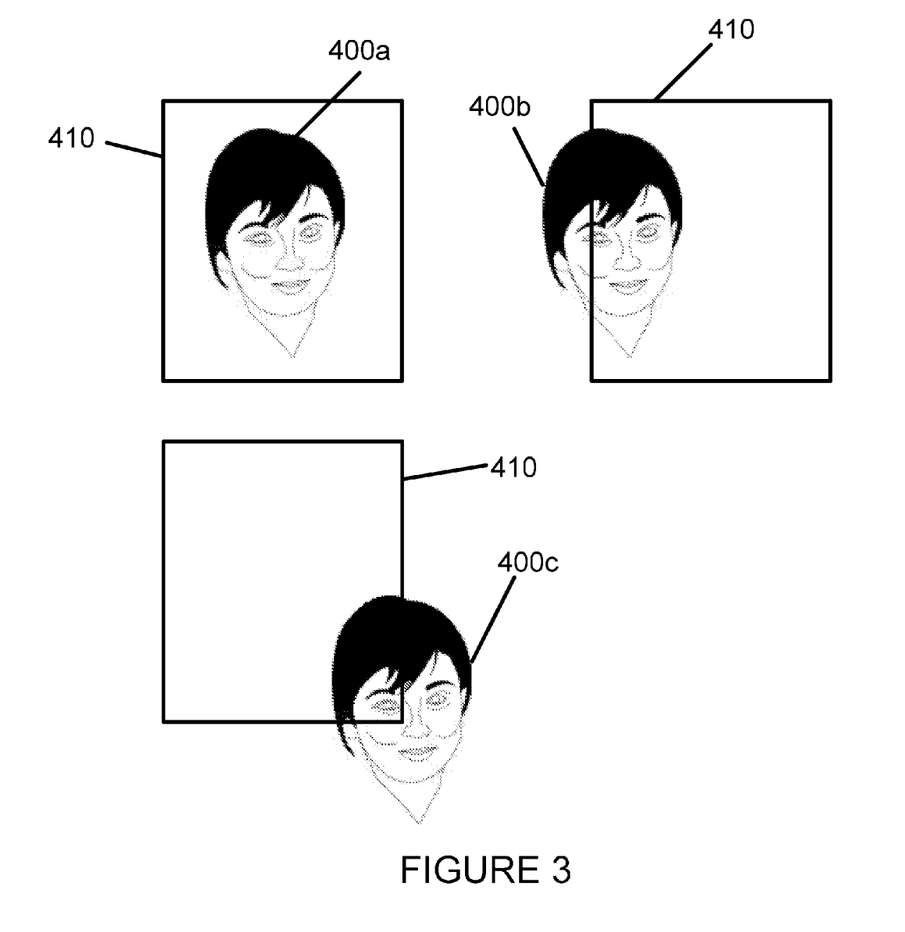
FIG. 3 is a depiction of a position determining process in accordance with an embodiment of the invention.

Analysis of the captured video in order to determine suspicious or malicious behavior will now be described in greater detail. As is shown in FIG. 3, a box 410 may be provided on a display viewable by a patient using the system. Indicator box 410 may further be provided as a circular or other appropriate indicator. Indicator box 410 may be further hidden from the view of the user. Alternatively a bezel or other edge of a smartphone, tablet computer, other mobile device, computer or the like may be used as a reference, i.e. as the "box." A representation of the patient's face may be shown in a position relative to an optimal filming position for the use of the system. Thus, while facial representation 400a is properly positioned, facial representation 400b is positioned to the left of indicator box 410, and facial representation 400c is positioned down and to the right of indicator box 410. The inventors of the present invention have determined that one indicator of suspicious or malicious behavior is the face of the patient leaving the field of view either a great number of times, and/or at one or more crucial times. Thus, if the patient's face leaves the display after placing a pill in their mouth, for example, but before showing that they have swallowed the pill, it may be that the patient is spitting out the pill. If their face leaves the display for one day, this may simply be user, but if it is determined that the patient's face is leaving the display on a consistent basis over time, suspicious or malicious behavior may be determined. Therefore, positions 400b and 400c may be designated as suspicious positions, and that upon this position being captured for a particular user at critical times over a number of administrations may result in flagging the participant for further review. Thus, an automated system for determining possible suspicious or malicious behavior is provided. The system may report such activity, or alternatively flag the patient to be more carefully looked after going forward.

In an alternative embodiment, a healthcare provider may have a reason to suspect a particular patient is acting suspiciously or maliciously, either by reviewing a recorded video of the patient taking their medication, or for any other reason. In this situation, it is contemplated in accordance with this embodiment of the invention that the healthcare provider is preferably able to indicate that the patient should be subject to an increased scrutiny. This indication may be made through a dashboard in which the healthcare provider can select a radio button or the like thus indicating this increased level of scrutiny, or otherwise make such an indication. Once flagged for additional scrutiny, a threshold for automatically determining suspicious or malicious behavior, such as the number of times a patient is able to have their face leave the screed before a warning is provided to the healthcare provider. Of course, this increased scrutiny may be applied to any of the suspicious or malicious activity recognition sequences described in accordance with this application, or to any other recognition sequences that may be employed.

Other visual motions or gestures that may be monitored for suspicious activities may include the moving of a hand to the patient's mouth after showing a pill in the mouth of the patient, indicating that the patient may be removing the pill. Once again, a one off situation may not be problematic, while consistent movement of the hand of the user in front of the mouth at a particularly sensitive time may warrant additional scrutiny, and a warning about suspicious or malicious behavior. Other movements of one or more body parts of the patient may also be included. Furthermore, audio indication of performing suspicious or malicious activity may be monitored, such as monitoring the user spitting out the pill. Such monitoring may automatically be performed based upon audio information, video information, or both. Other indications of malicious activity may include tracking a pill spit or thrown by the user across a screen, etc. Additionally, the pill or other medication may appear deformed to the camera. This may be from misuse or tampering by the user, and may indicate melting, tampering, cutting or opening the pill or tablet, r even emptying a capsule of its contents of medication before ingestion. Alignment of the portions of a capsule may also be analyzed. Thus, any noted deformation, color change, marking change or the like may be automatically determined by the system and reported to one or more monitors or key stakeholders.

If a monitor or other healthcare provider is provided a video review of one or more actions performed by a user of the system, it is contemplated in accordance with one or more embodiments of the invention that the monitor may be provided with a continuous one or more video clips for review. It is contemplated in accordance with one or more embodiments of the invention that if the system determines one or more video clips may include one or more suspicious activity actions, these video clips may be annotated automatically by the system, a risk estimate preferably being provided by the system, and correlated in accordance with a state of the user, the risk profile changing as the user moves through one or more different user states. Upon review of these video clips by the monitor or other healthcare provider, the user may further annotate the video by indicating further information along a timeline of video timestamps. This annotation is preferably further stored with the video for others to see, or for further analysis by the computer system in accordance with one or more embodiments of the invention. Based upon these annotations, and one or more other indicators of suspicious or malicious activity, one or more reports may be generated and one or more key stakeholders may be notified. Thus, the user may be classified into one or more categories based upon their activity, and based upon these categories, reported or further monitored as noted above.

Figure 4:
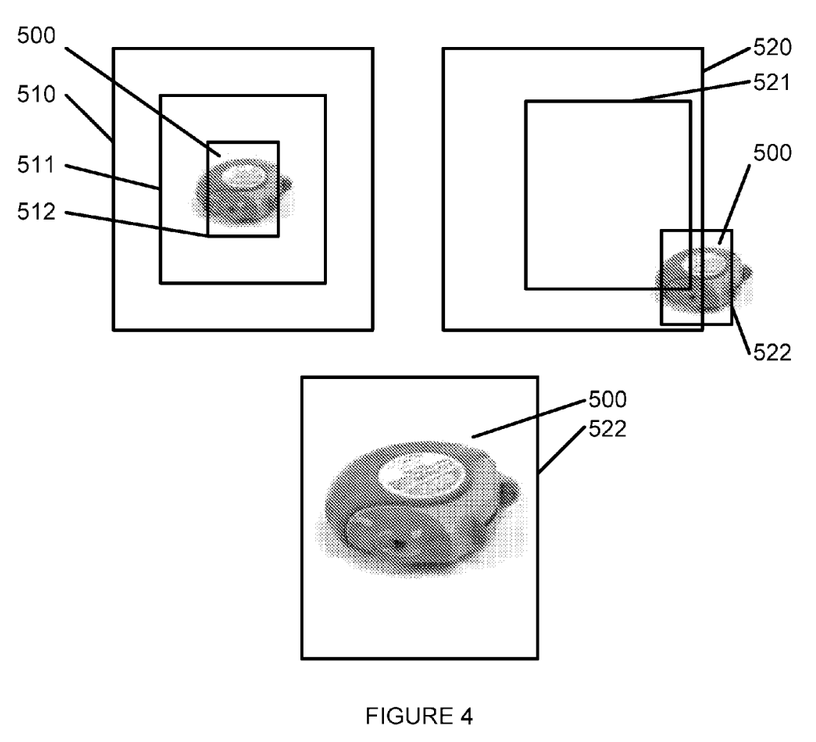
FIG. 4 is a depiction of another position determining process in accordance with an embodiment of the invention.

In addition to monitoring the movement of body parts, it is contemplated in accordance with the invention to monitor, either alone or in conjunction with the movement of the body parts, movement of one or more medication administration devices, such as an inhaler or injector mechanism. This may similarly apply to a cup or the like for administering a liquid medication, or a container for holding one or more pill, film or other oral medications. Therefore, as is shown in FIG. 4, in addition to tracking positioning of the patient, movement of one or more objects indicative of suspicious or malicious behavior, either absolutely or relative to another body part, may be determined. In the particular embodiment shown in FIG. 4, the positioning of an inhaler, glass of water, etc. relative to the display area, mouth, or face of the user may be employed. Similar tracking may be employed for an injectable medication delivery device, in accordance with yet another alternative embodiment of the invention. As is shown in FIG. 4, an inhaler 500 may be determined to be properly positioned in a box 522, the box being green, for example, as in the description of FIG. 4. Of course, the box need not be shown to the patient, in the manner noted above with respect to FIG. 3. Such an object, however, is more likely to be improperly positioned not only left to right and up to down, but also in distance to the imaging apparatus. Thus, in addition to a patient moving the apparatus off the display side to side or up and down, the patient may also move away from the imaging device in an attempt to trick the system. In such a manner the patient may be attempting to capitalize on one or more limitations of the imaging device, such as the resolution thereof, low light positions, and the like, and any affect such resolution might have on the ability of the imaging device to identify shape, color text or other coding, or the like associated with the object being imaged. Thus, if positioned too far away from the imaging apparatus, a sequence of boxes 510, 511, 512 and a small representation of inhaler 500 may be provided to alert the user to move the inhaler closer, or may be employed, while invisible to the patient, to determine whether an action has been properly determined as suspicious or malicious. Thus, if it is determined that the inhaler is not only too far away, but off center, boxes 520, 521, 522 may be provided (either visibly or not) to tack the position of the inhaler to determine any potential suspicious or malicious movements on the part of the patient.

Similar functionality may be provided for monitoring the position of an injectable apparatus relative to a user body part and display of the imaging apparatus to receive the injection, including relative angle and distance to the body part. Thus, as with the facial movement noted above with respect to FIG. 3, movement of the medication administration apparatus (inhaler or injectable) off the display (and thus out of view of the imaging apparatus), or away from the imaging apparatus to a point where the details of the medication administration apparatus are no longer discernible, may be monitored, and if performed multiple times over a predetermined timeframe, suspicious or malicious intention may be determined.

Figure 5:
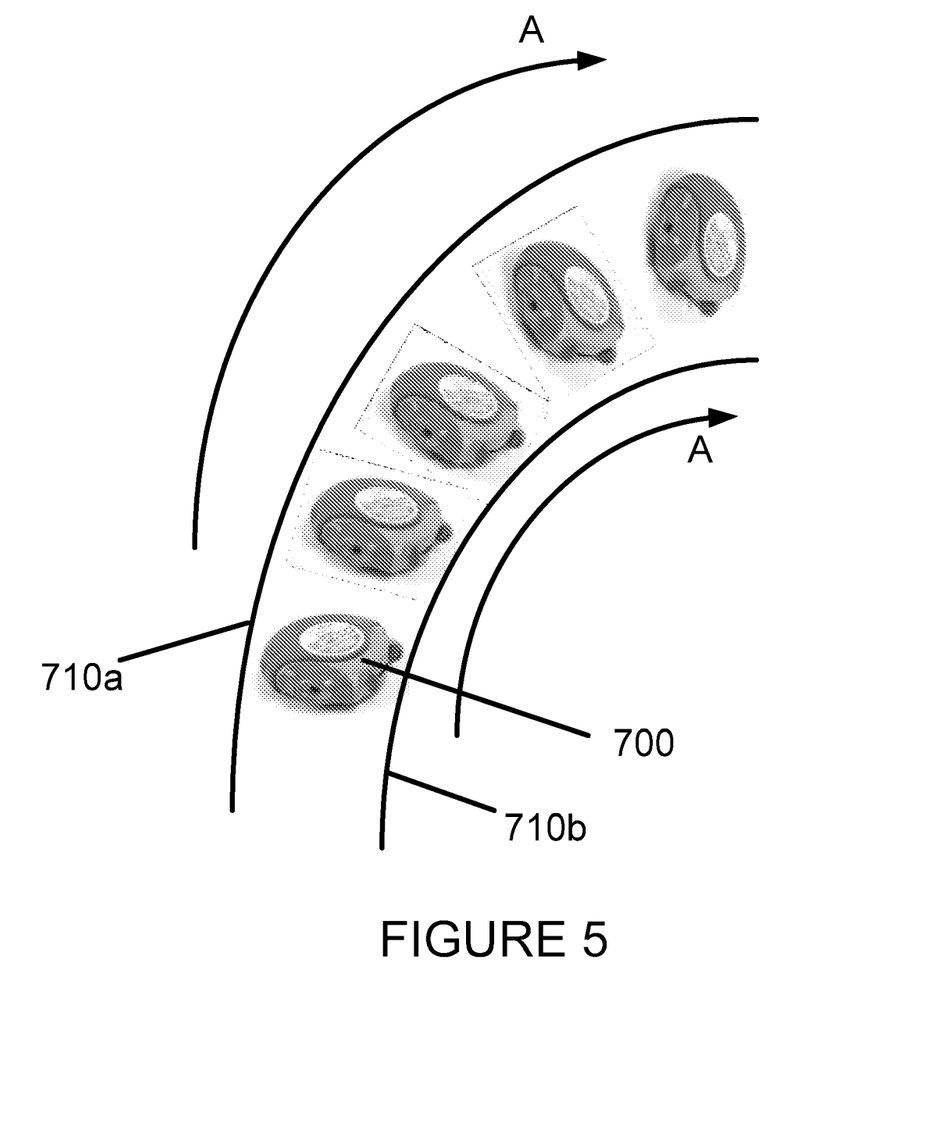
FIG. 5 is a depiction of a motion tracking process in accordance with an embodiment of the invention.

Furthermore, as is shown in FIG. 5, in addition to using absolute positioning of a medication administration apparatus, it is contemplated in accordance with the various embodiments of the invention that the movement of a medication administration apparatus 700 may be tracked, and thus any suspicious or malicious looking movements of the apparatus 700 may be determined. Thus, if the patient moves the apparatus too quickly, towards the edge of a field of view, towards an incorrect body part, faces the apparatus away from their mouth, or the like, suspicious or malicious behavior may be determined even thought the apparatus remains in the field of view at all times. Thus, as is show in FIG. 5, an administration apparatus 700 is indicated to be reoriented from a horizontal to a vertical orientation through movement in the direction noted by arrows A. A set of guidance tracks 710a, 710b may be displayed to a patient, or may be maintained apart from the patient display, and successive apparatus positions and orientations may be determined relative to the guidance tracks. As the apparatus moves along the proscribed path, proper location and orientation may be determined, while looking for any irregular movement possibly indicating suspicious or malicious behavior on the part of the patient. Thus, in accordance with an embodiment of the invention, if a virtual path is not properly followed by the patient moving such a medication administration apparatus, suspicious or malicious behavior may be determined As noted above, color and/or audio sequences may also be employed. Similar positioning information may be processed relative to an injectable medication.

In addition to determining suspicious or malicious activities taking place within a prescribed field of view of an imaging device, and during a time for monitoring medication adherence, various additional areas and times may be monitored in accordance with a preferred embodiment of the invention. In particular, it may be possible to continue to record before and after a medication administration time, thus attempting to determine if a user removes a pill from their mouth after they think monitoring has been completed, or before processing starts. If a user is to take multiple pills, for example, it is possible to continue to monitor the user between the administration, ingestion and the like of pills, even if the display is providing visual indications of which pill to take next, and is not displaying the face of the user. In addition, audio recording may be employed during these times to determine whether any sounds made by the user may be indicative of suspicious or malicious behavior. Such audio sounds may be indicative of the user spitting out a pill, actuating an inhaler or injectable device or the like. This monitored audio and video information may be automatically processed, in accordance with one or more other features of the invention, to determine whether this material provides additional evidence of suspicious or malicious behavior.

Finally, it may also be desirable to record a video field of view wider than that presented to the user n a display screen. Thus, if a wide angled view of a scene is imaged, a standard vide may be displayed to the user, and thus a user attempting to trick the system may think they are out of the field of view of the camera because they are not shown in the display, and may thus perform a suspicious or malicious act. If this act takes place within the field of view of the camera, even if not shown on the display, it may be analyzed or suspicious or malicious behavior.

Therefore, in accordance with various embodiments of the invention, because a video image of the patient actually administering an inhalable or other medication (or other method of medication administration, including but not limited to injections, dialysis, and any other medication administration procedure) may be captured and analyzed, analysis for suspicious or malicious behavior may be performed. As compared to a self reporting system or other available medication monitoring system, such as electronic medicine bottle caps, the various embodiments of the present invention are the only system that allow for the determination of one or more users trying to trick the system. This is because rather than simply relying on the patient to state that a particular medication was administered, the system makes an automated determination of proper administration. Through the accumulation of data, various motions, movements or sounds may be associated with suspicious or malicious behavior. It is only the various embodiments of the present invention that allow for this independent analysis of user activity.

Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are properly administering the medication according to the protocol, thus reducing the possibility of the potential appropriate movements considered to be "correct." Or, as noted above, capture of customized video sequences may be performed so that the user is more likely to repeat these same actions. Indeed, various instructional videos or other appropriate training may be provided to a user to insure they properly administer the medication. Thus, the level of water before and after drinking may be automatically analyzed, determination of one or more additional pills having been removed from a blister pack may be automatically performed, or injectables or inhalables may be automatically monitored to confirm consistent use, all through visual analysis of collected video sequences.

Once the video sequences are recorded and stored, preferably in a HIPAA compliant manner, further analysis may be performed thereon. For example, time on task may be measured for each portion of the medication administration sequence to be performed. In such a manner, it may be possible to determine how long a particular user takes to perform a portion of the medication administration sequence. Patterns may be determined to identify users who perform suspicious or malicious activity. For example, certain actions may be performed too quickly and uniformly over time, indicating a problem. As an example, in one particular embodiment of the invention, the user may be asked to drink a glass of water after ingesting a pill. If the time to drink the water is too consistently too fast, this may give evidence that the user is in fact not drinking the water, but rather is faking it to trick the system. Other time on task measurements may also be employed. Time stamp markers may thus be captured to confirm that the user is taking their medication at appropriate times and a number of times a user has taken a particular medication, to confirm whether there are substantial delays between instruction and administration, or for any other time sequence determination that may aid in determination of suspicious activity. Furthermore, other behavioral markers, such as, by way of example only, shaking hands indicating a nervousness, or other movements by a patient that may give a hint as to the physical or mental status thereof, and potential for trying to trick the system may be further employed.

The system may also preferably attempt to determine whether the use is employing a substitute or altered medication, such as if a pill appears dented or otherwise tampered with, has color changes, marking changes, texture changes, translucency changes, etc. A single or multiple consecutive or non-consecutive images may be employed in order to determine any changes in visual characteristics of the pill. Thus, confirming medication identity as well as determining deformation of, for example, a capsule (potentially indicative of taking the capsule apart to remove the medication) may be employed. In this particular embodiment of the invention, the ability to determined such malicious activity may be dependent on the resolution of the imaging device, the higher the resolution, the more complete a check for these issues may be performed. Therefore, it is contemplated in accordance with an embodiment of the invention that as the resolution of cameras improves, and as the processing power of mobile and other imaging devices increases, more complete checks may be employed.

This captured adherence information, including suspicious or malicious action information, may be provided to a healthcare provider, clinical trial manager or the like through a dashboard allowing for the review of information about an individual patient, entire population of patients, or demographically relevant information. Such information may be provided to easily notify the healthcare provider, clinical trial manager or the like of problem patients, demographic groups, medications or the like. One or more dashboards or other reporting mechanisms may be employed as described in copending U.S. patent application Ser. No. 13/189,518, filed Jul. 24, 2011 to Hanina et al., titled "Method and Apparatus for Monitoring Medication Adherence", the entire contents thereof being incorporated herein by reference. Thus, any suspicious or malicious activity information obtained in accordance with the present invention may be provided to one or more individuals in accordance with one or more methods or systems as described in the '518 application.

Further, once the information is captured to the dashboard, further analysis may be performed that may aid in determining potentially intentionally non-compliant users. For example, if the user has a high percentage of medication administration confirmations not employing the automated visual administration system (i.e. the user tells their healthcare provider over the phone that they took their medication, or otherwise indicate to the automated system that they took their medication without employing the automated system for confirmation), this may be indicative of an attempt to trick the system. Other such metrics may be employed and may preferably be gleaned from collected data for one or more particular patient populations. As noted above, any one or more of these situations may place the user in a different state or category, and may therefore justify additional scrutiny from the system and any monitors o healthcare providers. The user may be moved into or out of such state as noted above in accordance with actions they perform.

Through the use of suspicious and malicious activity tracking as described above, a type of administration language may be generated, allowing for extension to other patients, and also allowing for interpretation of reason for differences from a predefined sequence by a patient. Thus, if a patient performs an action differently over time, this difference may provide insight to a compliance failure, or active attempt to trick the system. It is further anticipated that analysis of large numbers of patients will allow for a more flexible system that may recognize more of a patient's suspicious or malicious movements, and thus may improve the ability of the system to function properly and identify these malicious patients trying to trick the system. Filters based upon these accumulated results may be employed to further identify potentially malicious users.

Therefore, in accordance with an embodiment of the invention, a user may be requested to perform a predetermined sequence of actions designed to ensure performance of medication administration, including medication ingestion of a pill or film based medication, inhalable or injectable medication, or the like. During administration, one or more actions associated with the administration may be monitored to determine one or more suspicious or malicious actions. These actions may comprise movement of the user out of the display of the imaging device, other movements associated with suspicious or malicious activity, such as the hand of a user covering their mouth at a critical time, indicating possible removal of the pill, coughing or the like at a critical time, or the like. These actions may be tracked over time to determine a habit of such action but the user to identify potential deliberate non-compliance. Such data from multiple users may be accumulated to determine a number of profiles that may be indicative of intentional non-compliance, and may be applied as filters to future action to categorize one or more users as high risk for intentional non-compliance. Video imaging of the users employing the system may further be stored for future analysis in order to determine time on task data, for example, to screen whether any particularly noticeable actions can be determined, such as the drinking of a glass of water in too fast a time, extremely consistent time for performing each action such that it is unlikely the user is actually taking the medication, or the like. Other metrics, such as a large number of manual skips, or other confirmations of medication administration not employing the inventive video medication administration system may also be indicative of a profile of a user that should be considered to further scrutiny.

Further uses of the video capture sequences may also be employed, including video capture of responses to questionnaires about current patient states of discomfort, informed consent, and the like which may be further used to determine whether a user is attempting to further trick the system. The patient may be able to send a video message answering one or more questions, the answers or any other motion or characteristic of the user when answering the questions may be further used to determine whether the user is attempting to trick the system.

In accordance with various embodiments of the invention, when considering administration of an inhalable or injectable medication, analysis of adherence video sequences may be employed to determine a likelihood that a patient has actually administered their medication, including one or more gestures of administration of the medication. Thus, based upon video and audio cues determined related to positioning and use of the medication administration apparatus, it may be determined that the patient is likely to be purposefully improperly positioning the apparatus, and therefore the system may indicate that it is possible that the patient has administered the medication intentionally improperly. Low confidence in proper administration based upon failure to properly position the apparatus, failure to record audio signals indicative of proper administration or the like may be employed to determine whether a patient should be further watched for additional future suspicious or malicious activity, via the automated training system described herein, by automated contact, or by individual personal contact. This determination of low confidence of administration, even if it is ultimately determined that administration likely took place, may still be utilized to classify the user as a potentially malicious user requiring greater scrutiny. Thus, the user may be classified as a good patient, a suspicious patient, malicious patient, etc., and may further provide one or more notifications to a monitor, healthcare provider, or sponsor (in the case of a clinical trial). Such notifications may comprise a dashboard notification (noted below), a text message, and automatically generated report or the like. Such confidence levels may be used, in accordance with a desired algorithm or the like, to provide an overall picture of medication administration by a patients or group of patients, thus allowing for further scrutiny based upon various characteristics of the patient population if it appears actions are changing, but not necessarily waiting until a critical issue is discovered.

It is further contemplated that the method and apparatus of the invention allow for integration with one or more audio or video conferencing systems, thus receiving and/or providing information there through. Thus, a user may employ a standard video conferencing tool or system, and have this information be coupled to a mobile or other device being used in accordance with an embodiment of the present invention.

In addition to processing user data locally in accordance with the imaging device, this information may be transmitted to a remote location for processing. Thus, in accordance with one or more embodiments of the invention, any and all processing noted herein may be performed locally, remotely, on in any combination as appropriate. The local device is therefore provided with a processor, imaging device and the like necessary to perform all actions necessary, including transmission and receipt of data from a remote location. Such transmission preferably takes place over a secure, encrypted transmission system with encrypted data. Similarly, any remote computing location preferably includes storage, processing and transmission and reception systems sufficient to receive, process and transmit secure data in accordance with the present invention. Thus communication between the local device and remote location is provided via a publically available network, private network or the like. Alternatively, data may be stored on the local device and transferred to the remote device as desired, or all processing may take place locally without any transmission of data to a remote location. Additionally, any type of camera may be employed, such as a camera included in a mobile device, tablet or laptop computer, cellular or smart phone and the like.

It is further contemplated in accordance with one or more embodiments of the invention that data provided from one or more of the above noted systems, sensors, cameras or the like may be combined with data from any one or more others to provided further information about suspicious activity. Thus, for example, synchronization of audio and video may provide an even better picture of malicious or suspicious behavior.

Furthermore, user of high resolution video images may also be employed. For example, if a user is determined to be at high risk for suspicious behavior, at one or more critical times during medication administration, higher resolution images may be obtained to allow for a greater level of scrutiny. By only retrieving these higher resolution images at the one or more critical times, overall processing requirements are reduced while allowing for a more complete review of user actions. Alternative, a plurality of captured lower resolution images may be combined to generate a high resolution image, using techniques such as Super Resolution or the like. In such a manner, higher resolution images are made available to review more critical portions of a medication administration sequence, while lower resolution images can be employed when suspicious activity is less likely.

In accordance with one or more embodiments of the present invention, the system in accordance with one or more embodiments of the invention will learn to recognize suspicious activity and may preferably attribute a scoring system based on different metrics. As noted above, as more patients are identified, profiles will be defined by the state machine and confidence levels attributed to patients who demonstrate these activities.

Various embodiments of the invention further include one or more automated processes for employing data mining/machine learning/AI techniques to provide a smarter system that can better classify patients, and then more easily monitor their medication administration over time. It is contemplated in accordance with the system that the system will be able to:

a) Understand the pattern of a patient with suspicious behavior b) Classify the current patient into different categories. Such as "Good user", "Suspicious User—need to be monitored", "Suspicious User—need to notify sponsor" and etc., thus placing the user into a particular state and driving the engagement of the system by the user in accordance with one or more attributes of that class.

c) Suggest a way to the human or even automatically implement a way (such as sending a text message) to alert the patient about the behavior based on his usage pattern.

The system preferably also provides one or more abilities to toggle between high res and low res images for capturing suspicious behaviors, as noted above. In particular this toggling may be performed by: 1) Capturing a high resolution image or a sequence of high resolution images at region of interest or time of interest to help check for suspicious behavior either by human or machine; 2) During other time or regions, low resolution images may be processed to make sure that the system can provide real-time feedback; and 3) capture low res images, and create a high res image from a serious of low res images for analysis on the server using techniques such Super Resolution.

Data captured by different sensors may also be fused to make a judgement whether the patient is suspicious. The fusing of different sources of data may include data captured by the system and other systems or patient information or history.

Therefore, in accordance with the invention, a method and apparatus are provided that allow for the automated confirmation of adherence to administration protocol for medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A medication administration confirmation apparatus, comprising:
    a display for displaying a first set of one or more instructions to a user encouraging proper performance of one or more steps of a medication administration sequence;
    a video capture device operable to capture one or more video sequences of a user administering medication in response to the displayed one or more instructions;
    an audio capture device operable to capture one or more audio sequences of the user administering medication;
    a memory operable to store the captured one or more video sequences and the captured one or more audio sequences; and
    a processor operable to analyze at least one of the stored video sequences to identify one or more predetermined indications of suspicious activity on behalf of the user, operable to mark the at least one of the stored video sequences as including suspicious activity, operable to analyze at least one of the stored audio sequences to determine one or more additional indications of suspicious activity on behalf of the user, and to cause the display to display one or more further instructions to the user encouraging proper performance of the one or more steps of the medication administration sequence in response to the identification of one or more predetermined indications of suspicious activity.

2. The medication confirmation apparatus of claim 1, wherein the processor is operable to output a prompt, to the user, to perform a particular sequence of actions to be stored as the one or more video sequences.

3. The medication confirmation apparatus of claim 1, wherein the one or more predetermined indications of suspicious activity comprises a face of the user leaving a field of view of the video capture device.

4. The medication confirmation apparatus of claim 1, wherein the one or more predetermined indications of suspicious activity comprises the hand of a user moving to their mouth.

5. The medication confirmation apparatus of claim 1, wherein the one or more additional indications of suspicious activity comprises the user coughing when a medication is in their mouth.

6. The medication confirmation apparatus of claim 1, wherein the processor is operable to record the audio sequence to the memory after the user has administered the medication.

7. The medication confirmation apparatus of claim 1, wherein the video capture device further comprises a display operable to display a first portion of a video being captured.

8. The medication confirmation apparatus of claim 7, wherein the processor is operable review a second portion of the captured video for suspicious behavior without outputting the second portion to the display.

9. The medication confirmation apparatus of claim 1, wherein the processor is operable to record the video sequence after the user has administered the medication.

10. The medication confirmation apparatus of claim 1, wherein the medication administration comprises ingestion of a pill.

11. The medication confirmation apparatus of claim 1, wherein the medication administration comprises ingestion of a dissolvable film.

12. The medication confirmation apparatus of claim 1, wherein the medication administration comprises actuation of an inhaler.

13. The medication confirmation apparatus of claim 1, wherein the medication administration comprises actuation of an injectable medication apparatus.

14. The medication confirmation apparatus of claim 1, wherein the processor is located at a remote location.

15. A medication administration confirmation apparatus, comprising:
    a display for displaying a first set of one or more instructions to a user encouraging proper performance of one or more steps of a medication administration sequence;
    a video capture device operable to capture one or more video sequences of a user administering medication;
    an audio capture device operable to capture one or more audio sequences of the user administering medication;
    a memory operable to store the captured one or more video sequences and the captured one or more audio sequences; and
    a processor operable to analyze at least one of the stored video sequences to determine one or more times on task for performance of one or more actions performed by the user during the medication administration, to analyze at least one of the stored audio sequences to determine one or more times on task for performance of one or more actions performed by the user during the medication administration, to analyze the determined one or more times on task to identify potentially suspicious behavior by the user, to track the occurrence of the identified potentially suspicious behavior by the user, to mark the at least one of the stored video sequences as including suspicious activity, and to cause the display to display one or more further instructions to the user encouraging proper performance of the one or more steps of the medication administration sequence in response to the identification of one or more predetermined indications of suspicious activity.

16. The medication administration confirmation apparatus of claim 15, wherein video sequences are captured and analyzed for a plurality of users, and wherein the processor is operable to define one or more filters applicable to a captured video sequence to determine suspicious activity therein in accordance with the analyzed video sequences from the plurality of users.

17. A method for confirming medication administration, comprising:

displaying, by a medication administration confirmation apparatus, a first set of one or more instructions to a user encouraging proper performance of one or more steps of a medication administration sequence;

capturing one or more video sequences of a user administering medication by a video capture device of the medication administration confirmation apparatus;

capturing one or more audio sequences of a user administering medication by an audio capture device of the medication administration confirmation apparatus;

storing the one or more of the captured video sequences and audio sequences to a nontransitory memory of the medication confirmation administration apparatus;

analyzing, by the medication administration confirmation apparatus, at least one of the one or more stored video sequences and at least one of the one or more audio sequences to identify one or more predetermined indications of suspicious activity on behalf of the user;

marking the at least one of the stored video sequences as including suspicious activity, and displaying, by the medication administration confirmation apparatus, one or more further instructions to the user encouraging proper performance of the one or more steps of the medication administration sequence in response to the identification of one or more predetermined indications of suspicious activity.

18. The method of claim 17, wherein analyzing the one or more stored video sequences further comprises:

identifying one or more predetermined indications of suspicious activity from a plurality of stored video sequences and audio sequences from a plurality of users;

generating a filter associated with one or more of the one or more identified predetermined indications of suspicious activity; and applying the filter to the at least one of the stored video sequences and audio sequences.

19. The method of claim 18, wherein the one or more predetermined indications of suspicious activity are selected from the group of the face of the user leaving a field of view of the video capture device, the hand of a user moving to their mouth, the user coughing when the pill is in their mouth, and the user spitting out the pill.

* * * * *

UNITED STATES PATENT AND TRADEMARK OFFICE
CERTIFICATE OF CORRECTION

PATENT NO. : 10,116,903 B2  
APPLICATION NO. : 13/831555  
DATED : October 30, 2018  
INVENTOR(S) : Adam Hanina, Lei Guan and Dehua Lai Page 1 of 1

It is certified that error appears in the above-identified patent and that said Letters Patent is hereby corrected as shown below:

On the Title Page

Column 2, Other Publications, Line 2:
Delete "Comgliance" and insert -- Compliance --, therefor.

Column 2, Other Publications, Line 3:
Delete "MDOT.asg." and insert -- MDOT.asp. --, therefor.

In the Claims

Column 23, Line 13, in Claim 17:
Delete "confirmation administration" and insert -- administration confirmation --, therefor.

Signed and Sealed this
Eighth Day of January, 2019

Andrei Iancu
*Director of the United States Patent and Trademark Office*